(12) United States Patent
Daniel

(10) Patent No.: US 9,649,217 B2
(45) Date of Patent: May 16, 2017

(54) IMPLANTABLE PENILE PROSTHETIC LOCKOUT VALVE ASSEMBLY

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 366 days.

(21) Appl. No.: 14/325,424

(22) Filed: Jul. 8, 2014

(65) Prior Publication Data

US 2016/0008162 A1    Jan. 14, 2016

(51) Int. Cl.
*A61F 5/41* (2006.01)
*A61F 2/26* (2006.01)

(52) U.S. Cl.
CPC .............. *A61F 5/41* (2013.01); *A61F 2/26* (2013.01); *A61F 2005/415* (2013.01)

(58) Field of Classification Search
CPC .......... A61B 17/3468; A61B 17/06066; A61B 17/04; A61B 2017/06052; A61F 2/26
USPC ..................................................... 600/38–41
See application file for complete search history.

(56) References Cited

U.S. PATENT DOCUMENTS

| | | |
|---|---|---|
| 3,533,719 A | 10/1970 | Cobarg et al. |
| 3,734,258 A | 5/1973 | Roob |
| 3,853,122 A | 12/1974 | Bloomberg et al. |
| 3,954,102 A | 5/1976 | Buuck |
| 4,224,934 A | 9/1980 | Scott et al. |
| 4,267,829 A | 5/1981 | Burton et al. |
| 4,335,714 A | 6/1982 | Edgerton et al. |
| 4,342,308 A | 8/1982 | Trick |
| 4,353,360 A | 10/1982 | Finney et al. |
| 4,360,010 A | 11/1982 | Finney |
| 4,364,379 A | 12/1982 | Finney |
| 4,383,525 A | 5/1983 | Scott et al. |
| 4,407,278 A | 10/1983 | Burton et al. |
| 4,424,807 A | 1/1984 | Evans et al. |
| 4,441,491 A | 4/1984 | Evans et al. |
| 4,449,520 A | 5/1984 | Palomar et al. |
| 4,545,081 A | 10/1985 | Nestor et al. |
| 4,548,081 A | 10/1985 | Wolthausen |

(Continued)

FOREIGN PATENT DOCUMENTS

| | | |
|---|---|---|
| CA | 2824259 | 3/2014 |
| DE | 3836787 C2 | 5/1990 |

(Continued)

OTHER PUBLICATIONS

Office Action mailed on May 18, 2016 in U.S. Appl. No. 14/304,984.

(Continued)

*Primary Examiner* — Samuel Gilbert
(74) *Attorney, Agent, or Firm* — Coloplast Corp., Coloplast A/S; Nick Baumann

(57) ABSTRACT

A lockout valve assembly of an implantable penile prosthetic includes a body and a lockout valve. The body is attachable between a reservoir and a pump of the implantable penile prosthetic. The lockout valve includes a core rotatably disposed inside the body, an inflation channel formed through a portion of the core, a deflation pathway separate from the inflation channel and formed through a diameter of the core, and a one-way check valve disposed in the deflation pathway of the core.

17 Claims, 13 Drawing Sheets

(56) References Cited

U.S. PATENT DOCUMENTS

| | | | |
|---|---|---|---|
| 4,559,931 A | 12/1985 | Fischell | |
| 4,566,446 A | 1/1986 | Fogarty | |
| 4,572,168 A | 2/1986 | Fischell | |
| 4,576,234 A | 3/1986 | Upchurc | |
| 4,584,994 A | 4/1986 | Bamberger et al. | |
| 4,594,997 A | 6/1986 | Hakky | |
| 4,596,242 A | 6/1986 | Fischell | |
| 4,671,261 A * | 6/1987 | Fischell | A61F 2/26 600/40 |
| 4,682,583 A | 7/1987 | Burton et al. | |
| 4,682,589 A | 7/1987 | Finney | |
| 4,816,016 A | 3/1989 | Schulte et al. | |
| 4,846,909 A | 7/1989 | Klug et al. | |
| 4,982,731 A | 1/1991 | Lue et al. | |
| 5,010,882 A | 4/1991 | Polyak et al. | |
| 5,062,417 A | 11/1991 | Cowen | |
| 5,067,485 A | 11/1991 | Cowen | |
| 5,101,813 A | 4/1992 | Trick | |
| 5,133,923 A | 7/1992 | Klug | |
| 5,141,509 A | 8/1992 | Burton et al. | |
| 5,159,920 A | 11/1992 | Condon et al. | |
| 5,160,341 A | 11/1992 | Brenneman et al. | |
| 5,167,611 A | 12/1992 | Cowan | |
| 5,188,596 A | 2/1993 | Condon et al. | |
| 5,250,020 A | 10/1993 | Bley | |
| 5,254,092 A | 10/1993 | Polyak | |
| 5,263,946 A | 11/1993 | Klug | |
| 5,454,798 A | 10/1995 | Kubalak et al. | |
| 5,558,829 A | 9/1996 | Petrick | |
| 5,584,271 A | 12/1996 | Sakata | |
| 5,632,777 A | 5/1997 | Petrick | |
| 5,653,757 A | 8/1997 | Petrick | |
| 5,704,895 A | 1/1998 | Scott et al. | |
| 5,725,507 A | 3/1998 | Petrick | |
| 5,779,964 A | 7/1998 | Welch et al. | |
| 5,851,176 A | 12/1998 | Willard | |
| 5,895,424 A | 4/1999 | Steele et al. | |
| 5,919,170 A | 7/1999 | Woessner | |
| 5,935,362 A | 8/1999 | Petrick | |
| 6,039,750 A | 3/2000 | Kubalak et al. | |
| 6,060,639 A | 5/2000 | Petrick | |
| 6,171,233 B1 | 1/2001 | Willard | |
| 6,443,887 B1 | 9/2002 | Derus et al. | |
| 6,475,137 B1 | 11/2002 | Elist | |
| 6,533,719 B2 | 3/2003 | Kuyava et al. | |
| 6,537,192 B1 | 3/2003 | Elliott et al. | |
| 6,572,527 B2 | 6/2003 | Steele et al. | |
| D476,471 S | 7/2003 | Alfaro | |
| 6,599,231 B1 | 7/2003 | Elliott et al. | |
| 6,616,593 B1 | 9/2003 | Elliott et al. | |
| 6,638,211 B2 | 10/2003 | Suslian et al. | |
| 6,639,237 B2 | 10/2003 | Pedersen et al. | |
| 6,656,107 B1 | 12/2003 | Pedersen et al. | |
| 6,682,471 B2 | 1/2004 | Steele et al. | |
| 6,723,042 B2 | 4/2004 | Almli et al. | |
| 6,730,017 B2 | 5/2004 | Henkel et al. | |
| D496,727 S | 9/2004 | Kubalak et al. | |
| D496,993 S | 10/2004 | Kubalak et al. | |
| D497,205 S | 10/2004 | Kubalak et al. | |
| 6,805,690 B2 | 10/2004 | Ogden et al. | |
| 6,808,489 B2 | 10/2004 | George et al. | |
| 6,869,390 B2 | 3/2005 | Elliott et al. | |
| 6,887,230 B2 | 5/2005 | Kubalak et al. | |
| 6,895,998 B2 | 5/2005 | Aoki et al. | |
| D508,128 S | 8/2005 | Kubalak et al. | |
| 6,935,847 B2 | 8/2005 | Kuyava et al. | |
| 6,953,426 B2 | 10/2005 | Barber et al. | |
| 6,991,601 B2 | 1/2006 | Kuyava et al. | |
| 7,001,307 B2 | 2/2006 | Matsunaga et al. | |
| 7,066,878 B2 | 6/2006 | Eid | |
| 7,229,400 B2 | 6/2007 | Elliott et al. | |
| 7,244,227 B2 | 7/2007 | Morningstar | |
| 7,250,026 B2 | 7/2007 | Kuyava | |
| 7,350,538 B2 | 4/2008 | Kuyava et al. | |
| 7,438,682 B2 | 10/2008 | Henkel et al. | |
| 7,494,495 B2 | 2/2009 | Delorme et al. | |
| 7,588,598 B2 | 9/2009 | Delorme et al. | |
| 7,946,975 B2 | 5/2011 | George et al. | |
| 7,996,092 B2 | 8/2011 | Mrva et al. | |
| 8,016,746 B2 | 9/2011 | Ellering | |
| 8,109,870 B2 | 2/2012 | Kuyava et al. | |
| 8,276,591 B2 | 10/2012 | Henkel et al. | |
| 8,337,392 B2 | 12/2012 | Morningstar | |
| 8,585,580 B2 | 11/2013 | Vaingast et al. | |
| 2002/0082473 A1 | 6/2002 | Henkel et al. | |
| 2002/0082709 A1 | 6/2002 | Almli et al. | |
| 2003/0065249 A1 | 4/2003 | Kuyava et al. | |
| 2004/0220447 A1 | 11/2004 | Morningstar | |
| 2004/0220448 A1 | 11/2004 | Henkel et al. | |
| 2004/0225182 A1 | 11/2004 | Eid | |
| 2004/0249397 A1 | 12/2004 | Delorme et al. | |
| 2004/0249473 A1 | 12/2004 | Delorme et al. | |
| 2005/0010945 A1 | 1/2005 | Hayashi | |
| 2005/0027252 A1 | 2/2005 | Boukas | |
| 2005/0028418 A1 | 2/2005 | Pargman | |
| 2005/0075529 A1 | 4/2005 | Pedersen et al. | |
| 2005/0131274 A1 | 6/2005 | Suslian et al. | |
| 2005/0209499 A1 | 9/2005 | Elliott et al. | |
| 2005/0250981 A1 | 11/2005 | Kuyava et al. | |
| 2005/0267320 A1 | 12/2005 | Barber et al. | |
| 2005/0278037 A1 | 12/2005 | Delorme et al. | |
| 2005/0288692 A1 | 12/2005 | Beraud et al. | |
| 2006/0003190 A1 | 1/2006 | Abarra et al. | |
| 2006/0012252 A1 | 1/2006 | Miyata et al. | |
| 2006/0025753 A1 | 2/2006 | Kubalak et al. | |
| 2006/0063960 A1 | 3/2006 | Wissman et al. | |
| 2006/0135845 A1 | 6/2006 | Kuyava et al. | |
| 2006/0173468 A1 | 8/2006 | Simmon et al. | |
| 2006/0224039 A1 | 10/2006 | Steele | |
| 2007/0135673 A1 | 6/2007 | Elliott et al. | |
| 2007/0142700 A1 | 6/2007 | Fogarty et al. | |
| 2011/0118540 A1 | 5/2011 | Morningstar | |
| 2012/0022323 A1 | 1/2012 | Forsell | |
| 2013/0072751 A1 | 3/2013 | Fogarty | |

FOREIGN PATENT DOCUMENTS

| | | |
|---|---|---|
| EP | 0093507 B1 | 11/1983 |
| FR | 2556585 B1 | 6/1985 |
| GB | 1549315 A | 7/1979 |
| WO | 9114409 A1 | 10/1991 |
| WO | 9634581 A1 | 11/1996 |
| WO | 9804214 A1 | 2/1998 |
| WO | 2006066199 A1 | 6/2006 |
| WO | 2007073556 A2 | 6/2007 |
| WO | 2009024024 A1 | 2/2009 |
| WO | 2009094431 A4 | 11/2009 |
| WO | 2012139589 A1 | 10/2012 |

OTHER PUBLICATIONS

American Medical System, AMS 800TM Urinary Control System Operating Room Manual, 2004.
International Search Report and Written Opinion issued in PCT/DK2011/050031, mailed Mar. 16, 2011, 5 pages.
International Search Report and Written Opinion issued in PCT/DK2012/000090, mailed Sep. 6, 2013, 16 pages.
Office Action From DK Patent Office Mailed Jun. 23, 2010, 5 pages.

* cited by examiner

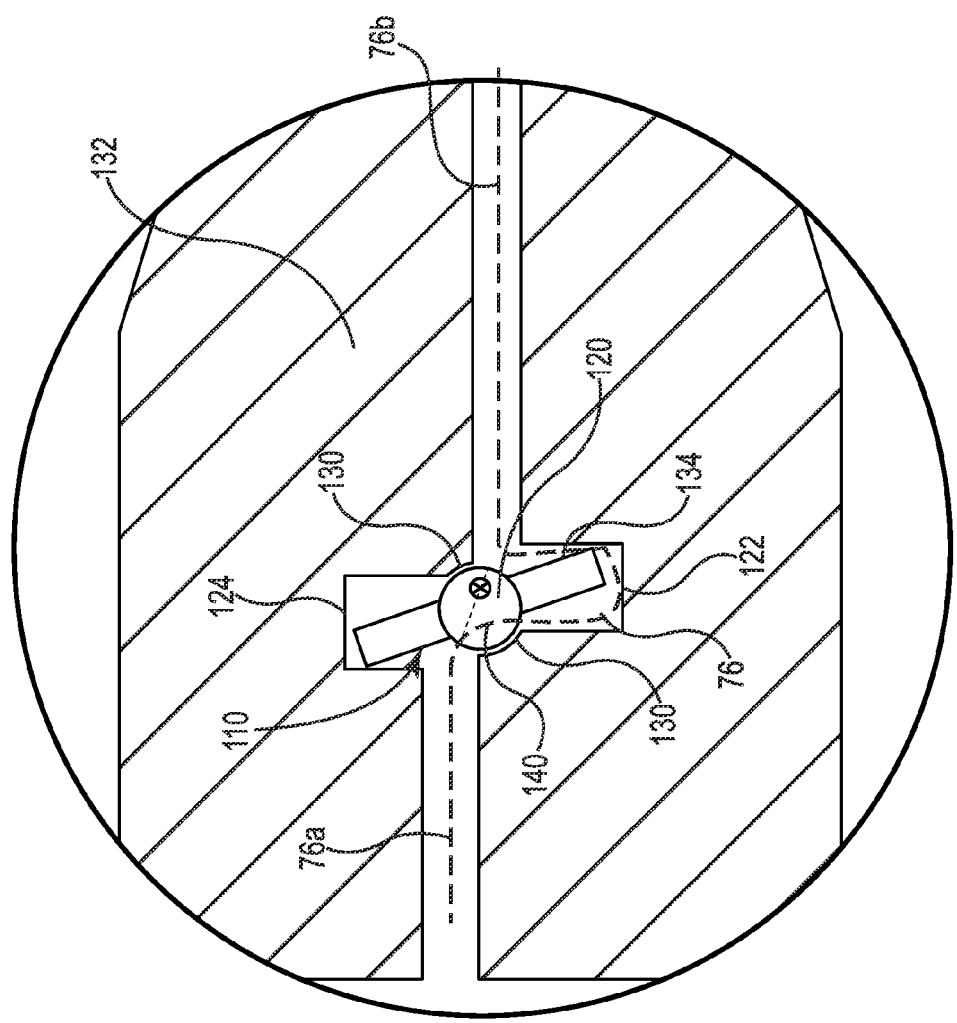

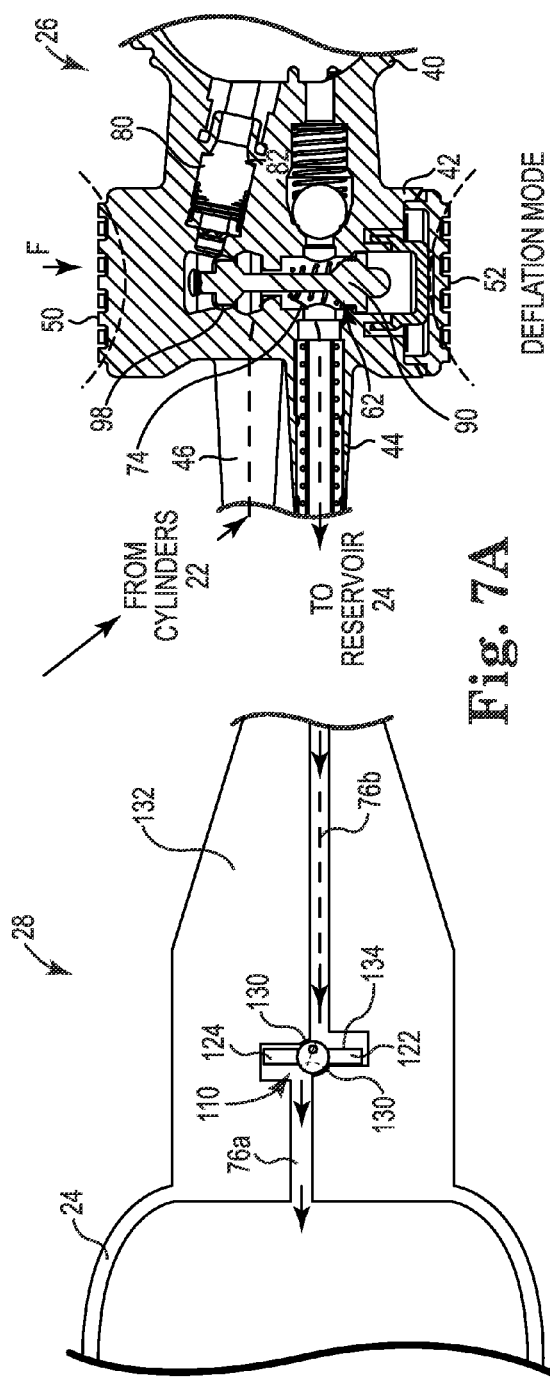
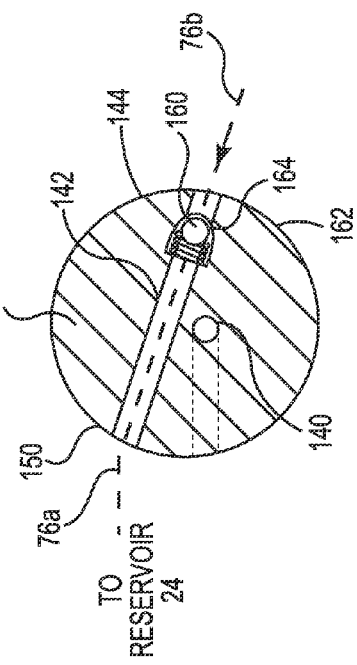
Fig. 7A
Fig. 7B

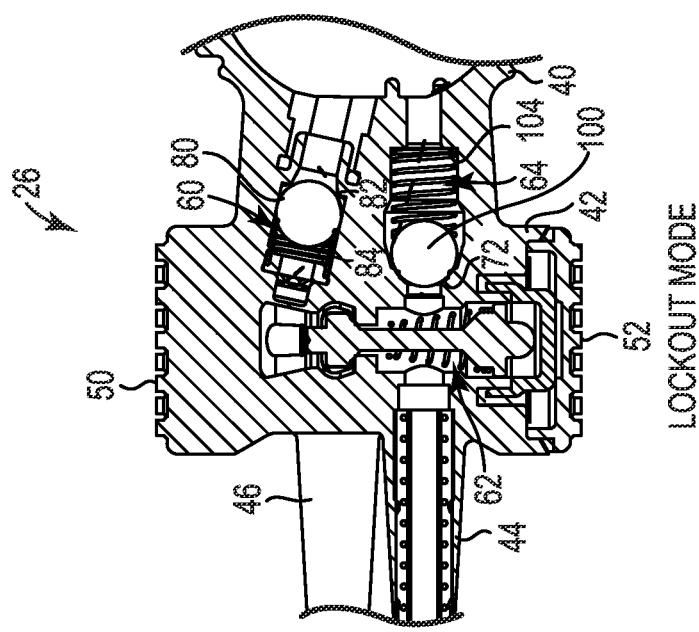
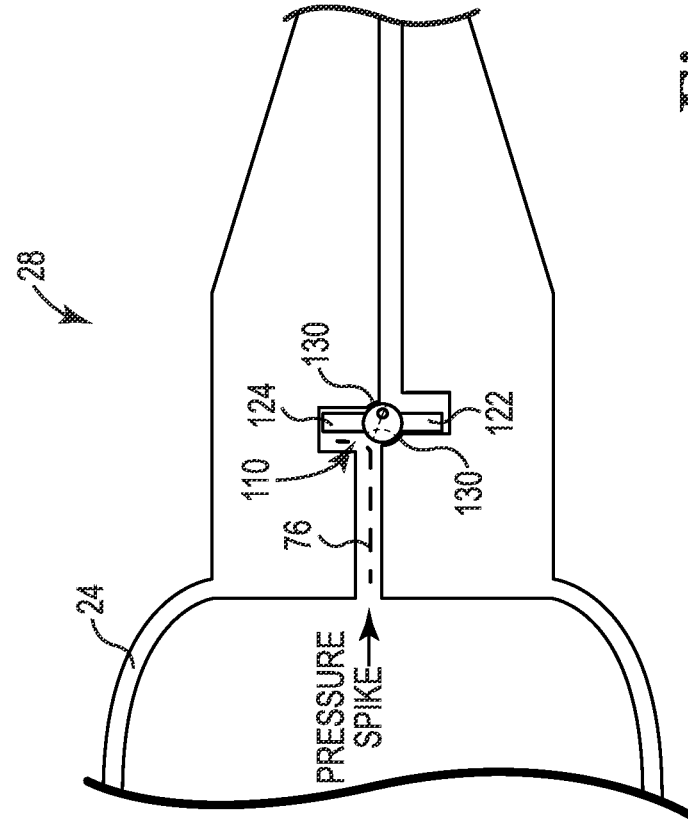
Fig. 8

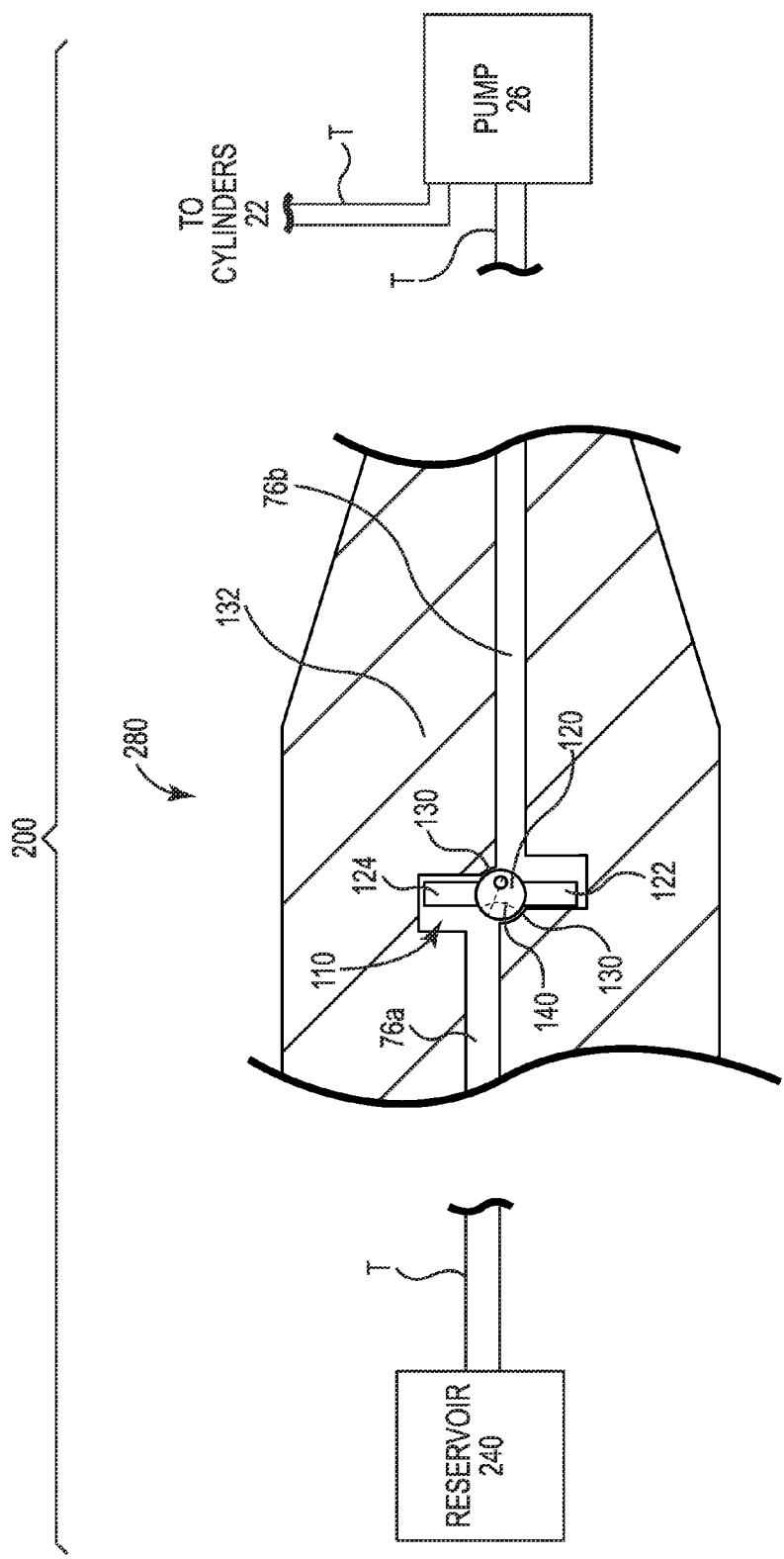

IMPLANTABLE PENILE PROSTHETIC LOCKOUT VALVE ASSEMBLY

BACKGROUND

An implanted penile prosthetic is a proven approach to relieve erectile dysfunction in men.

A penile prosthetic typically includes two cylinders that are implanted in the corpora cavernosa of the penis, a reservoir implanted in the abdomen that communicates with the cylinder(s), and a pump, often located in the scrotum, that is employed to move liquid from the reservoir into the cylinder(s).

In a typical application, the user squeezes a bulb of the pump multiple times to transfer liquid from the reservoir to the cylinders. Each squeeze of the bulb ejects some liquid to the cylinders. The squeezed (compressed) bulb recovers, creating a suction pressure that draws liquid out of the reservoir and into the bulb. Subsequent squeezing and recovery of the bulb transfers liquid from the reservoir into the cylinders, which inflates the cylinders to provide the user with an erect penis. The user may return the penis to its flaccid state by selectively activating a deflation mechanism and transferring the liquid from the cylinder(s) back into the reservoir.

It is desirable to provide the user with a simple and efficient mechanism for addressing erectile dysfunction.

SUMMARY

One aspect provides a lockout valve assembly of an implantable penile prosthetic having a body and a lockout valve. The body is attachable between a reservoir and a pump of the implantable penile prosthetic. The lockout valve includes a core rotatably disposed inside the body, an inflation channel formed through a portion of the core, a deflation pathway separate from the inflation channel and formed through a diameter of the core, and a one-way check valve disposed in the deflation pathway of the core.

One aspect provides an implantable penile prosthetic with a pump attachable to a cylinder and a reservoir, and a lockout valve assembly attachable between the reservoir and the pump. The lockout valve assembly has a lockout valve rotatably disposed in a body of the lockout valve assembly. The lockout valve includes a spherical part, an inlet flange connected to and extending radially away from the spherical part, a lockout flange connected to and extending radially away from the spherical part, an inflation channel formed through a portion of the spherical part, a deflation pathway formed in the spherical part separate from the inflation channel, and a one-way check valve disposed in the deflation pathway of the spherical part.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

FIG. 6B is a view of the lockout valve assembly illustrated in FIG. 6A with the pump in the inflation mode.

FIG. 7A is a cross-sectional view of portions of the penile prosthetic with the pump in a deflation mode for deflating the cylinders.

FIG. 7B is a view of the lockout valve assembly illustrated in FIG. 7A with the pump in the deflation mode.

FIG. 8 is a cross-sectional view of portions of the penile prosthetic with the pump and the lockout valve assembly in a lockout mode for deflating the cylinders.

FIG. 10 is perspective view of a lockout valve assembly provided separate from a reservoir and separate from a pump of a penile prosthetic.

DETAILED DESCRIPTION

Figure 1:
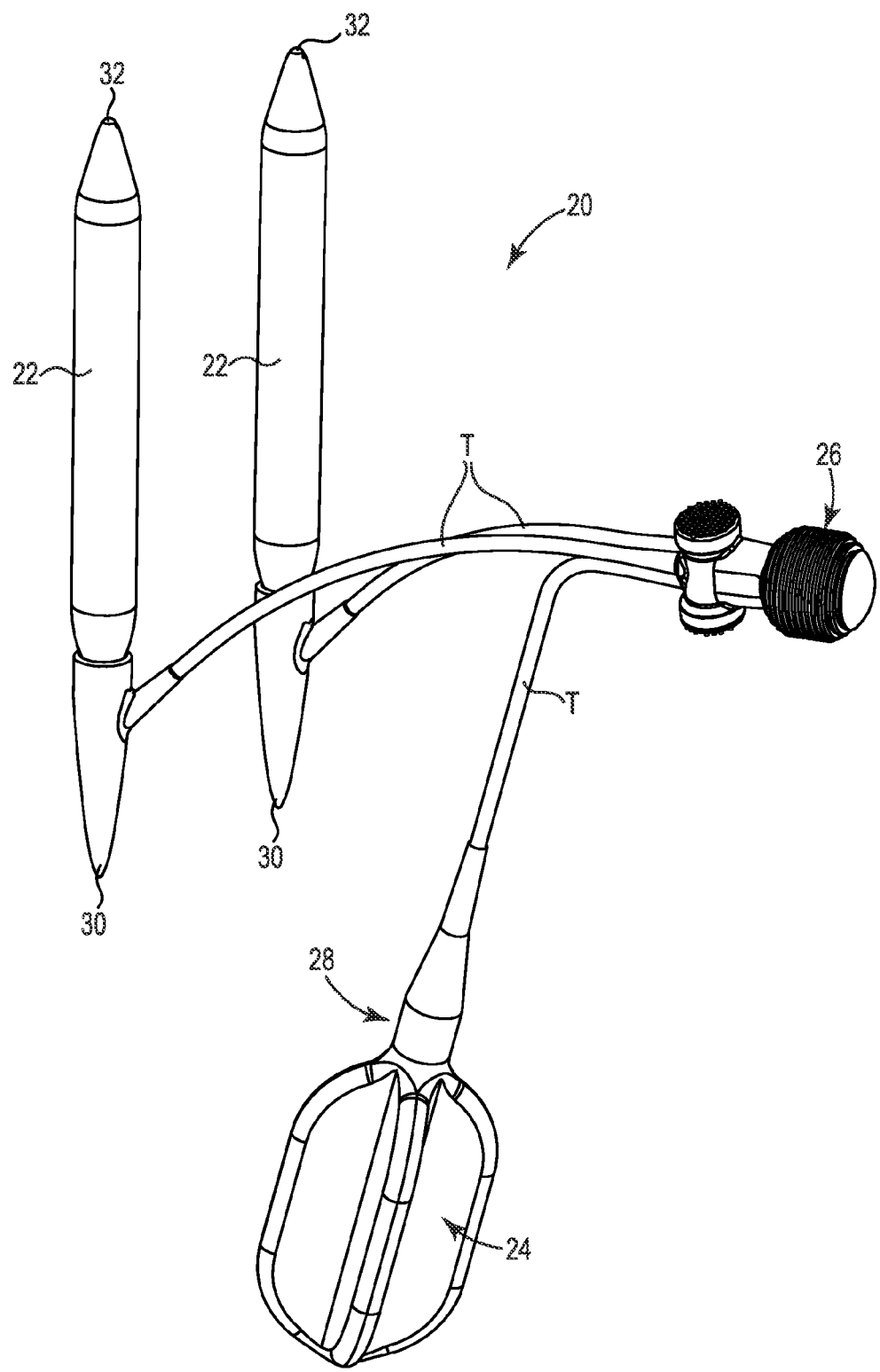
FIG. 1 is a perspective view of one embodiment of a penile prosthetic having a pump that has been connected to a pair of penile cylinders and a reservoir.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

The term "hemisphere" in this application means half of a sphere. One example of a half of a sphere is either the top half or the bottom half on either side of an equator of the sphere. Another example of a half of a sphere is either the left (west) half or the right (east) half on either side of a meridian of the sphere (a longitudinal line extending north-to-south).

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

The term "pressurized" means that a pressure greater than atmospheric pressure is exerted on a fluid. The fluid is said to be pressurized. Atmospheric pressure at sea level is approximately 14 pounds per square inch (PSI).

A penile prosthetic includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir. Pressure spikes delivered unintentionally to the reservoir can result in a stream of pressurized liquid undesirably flowing from the reservoir directly to the cylinders.

"Autoinflation" means an involuntary inflation of a cylinder implanted in a penis. Autoinflation occurs when the pressure of the liquid in the reservoir is increased sharply, for example by the user leaning against a table and pressurizing the reservoir implanted in the abdomen. The increase in the reservoir pressure can cause the liquid to flow and bypass the pump bulb, resulting in directly inflating the cylinders. The consequence is an unintended and undesirable erection of the penis.

Embodiments provide a penile prosthetic having a lockout valve assembly that is configured to prevent a stream of pressurized liquid from undesirably flowing from the reservoir directly to the cylinders.

Embodiments provide a lockout valve located between a reservoir and a pump in a penile prosthetic. In one embodiment, the lockout valve assembly is integrated with the reservoir downstream from a liquid holding receptacle of the reservoir.

FIG. 1 is a perspective view of one embodiment of an assembled penile prosthetic 20. The penile prosthetic 20 is provided to the healthcare facility in several parts that are assembled by a surgeon into a working unit during implantation. As manufactured, the penile prosthetic 20 includes cylinders 22 that are implantable into a penis, a reservoir 24, a pump 26 that is attachable between the cylinders 22 and the reservoir 24, for example by suitable implantable tubing T, and a lockout valve assembly 28. In one embodiment, the lockout valve assembly 28 is integrated as one monolithic piece with the reservoir 24.

The lockout valve assembly 28 operates to allow the pump 26 to draw liquid from the reservoir 24 and deliver the liquid into the cylinders 22 to provide the user with an erection. The lockout valve assembly 28 also operates to allow the cylinders 22 to be deflated by draining the liquid from the cylinders 22 back into the reservoir 24. One beneficial feature of the lockout valve assembly 28 is to prevent the unintended pressurization of liquid in the reservoir 24 from undesirably, and unintentionally, inflating the cylinders 22 and causing an unintended erection.

Each of the cylinders 22 includes a proximal end 30 opposite a distal end 32. During implantation, the proximal end 30 (also called a rear tip) is implanted toward the crus of the penis and the distal end 32 is implanted within the glans penis. The cylinders 22 are fabricated from material configured to collapse when the cylinders 22 are deflated to provide the penis with a flaccid state and expand when the cylinders 22 are inflated with liquid to provide the penis with an erection. As a point of reference, the cylinders 22 are illustrated in an inflated state. Suitable material for fabricating the cylinders 22 includes silicone, biocompatible polymers such as urethanes, and blends of polymers with urethane, copolymers of urethane, or the like. Suitable cylinders are available from Coloplast Corp., Minneapolis, Minn.

The reservoir 24 provides a receptacle that is sized to maintain a volume of liquid between about 50-300 ml. In one embodiment, the reservoir 24 is provided as a "cloverleaf" style of reservoir having multiple leafs that may be folded one against the other to compact the reservoir 24 for implantation into the abdomen of the user. One suitable reservoir 24 is sized to retain approximately 130 mL of liquid and is available from Coloplast Corp., Minneapolis, Minn.

Figure 2:
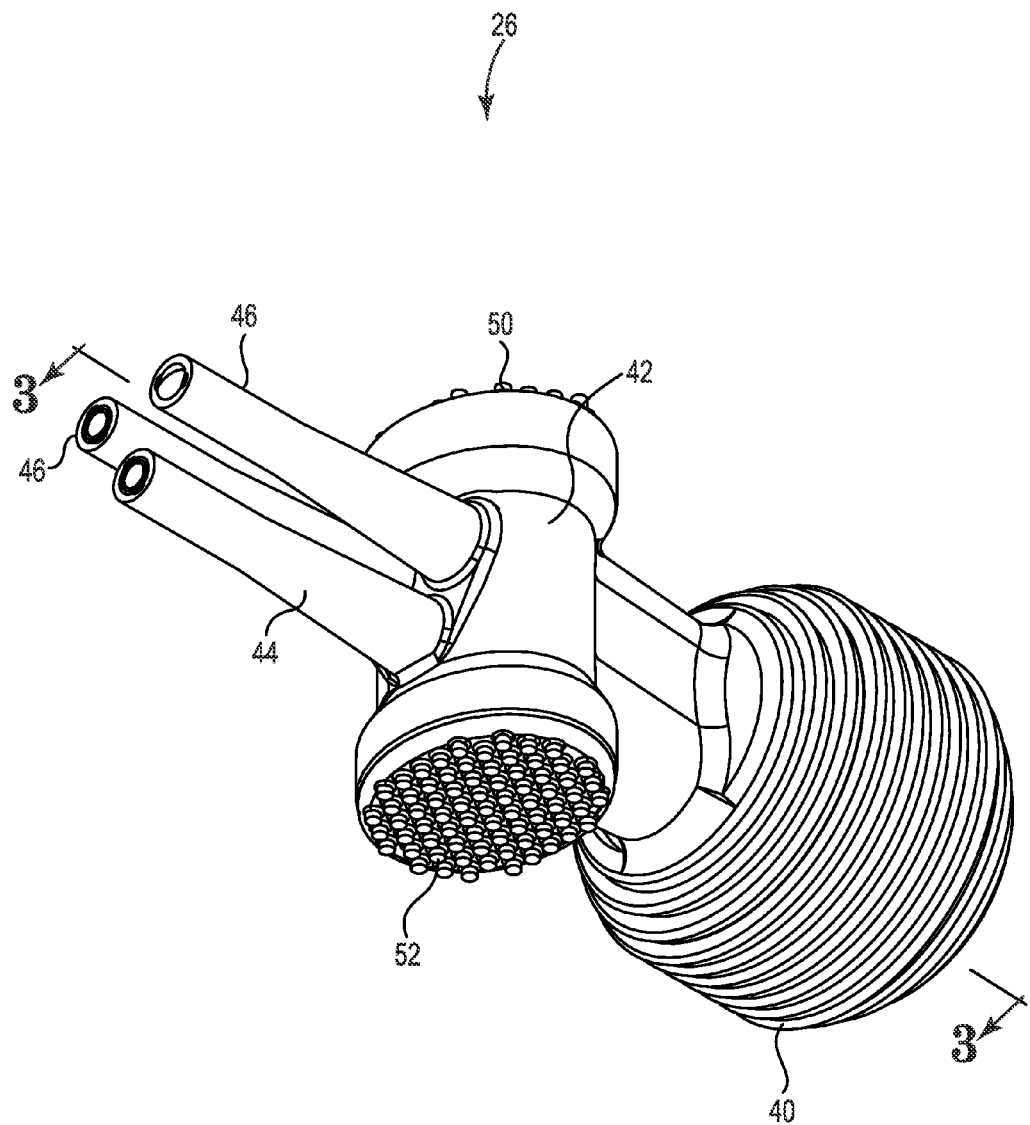
FIG. 2 is a perspective view of the pump illustrated in FIG. 1.

FIG. 2 is a perspective view of the pump 26. The pump 26 includes a pump bulb 40, a pump body 42, an inlet tube 44 connected between the reservoir 24 and the pump body 42, and a pair of exhaust tubes 46 connected between the pump body 42 and the cylinders 22.

With reference to FIG. 1, the pump bulb 40 is flexible and includes a ribbed accordion structure that allows the pump bulb 40 to collapse when squeezed to drive liquid out of the pump bulb 40, through the pump body, and out of the exhaust tubes 46 to the cylinders 22. The accordion structure provides a grasping surface and allows the pump bulb 40 to recover after being squeezed, which results in an expansion of the bulb 40. Expansion of the pump bulb 40 creates a negative local pressure in the bulb 40 that draws liquid out of the reservoir 24 (FIG. 1), through the inlet tube 44 and the pump body 42, and into the pump bulb 40. Subsequent squeezing and recovery of the pump bulb 40 ejects liquid from the pump bulb 40, and draws liquid back into the pump bulb 40 in a cyclical manner.

In one embodiment, the pump body 42 is integrally formed and connected with the pump bulb 40 and includes a first activation surface 50 opposite a second activation surface 52. The activation surfaces 50, 52 (also called deflation pads) are illustrated as non-circular (elliptical) although other shapes for the activation surfaces 50, 52 are also acceptable. The pump body 42 houses or maintains valves (described below) that may be activated/deactivated by pressing the activation surfaces 50, 52.

The inlet tube 44 is connected to the reservoir 24 (FIG. 1) by the tubing T. Each of the exhaust tubes 46 is connected to a respective one of the cylinders 22 via the tubing T. Compressing the pump bulb 40 ejects the liquid from the bulb 40 through the exhaust tubes 46 to the cylinders 22, and expansion of the pump bulb 40 creates suction that draws liquid from the reservoir 24 through the pump body 42 and the inlet tube 44 at a low velocity for delivery into the pump bulb 40.

Generally, the pump 26 is implanted into the scrotum of the user and connected to the cylinders 22 that are implanted into the penis of the user. The reservoir 24 is connected to the cylinders 22 and to the pump 26, and implanted within the abdomen of the user after verification that the connections are leak-free. The pump 26 is fabricated from material suitable for body implantation, such as silicone or the urethane-based materials described above for the cylinders 22 or the reservoir 24.

Figure 3:
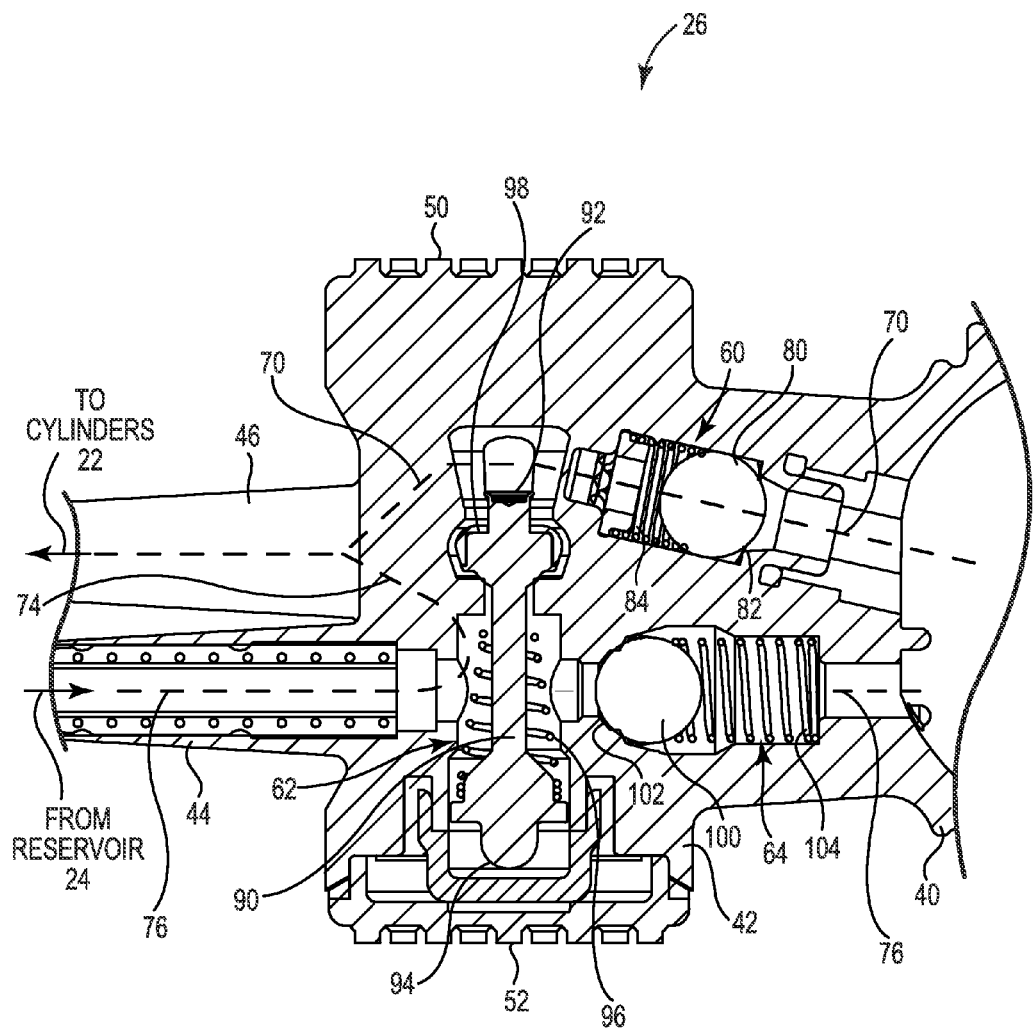
FIG. 3 is a vertical cross-sectional view taken centrally between deflation pads of the pump illustrated in FIG. 1.

FIG. 3 is a vertical cross-sectional view of the pump 26 taken centrally between the pair of exhaust tubes 46 top-to-bottom between the deflation pads 50, 52. The pump 26 includes an exhaust valve assembly 60 located between the pump bulb 40 and the cylinders 22, a deflation valve assembly 62 located between the deflation pads 50, 52, and an inlet valve assembly 64 located between the reservoir 24 and the pump bulb 40.

The exhaust valve assembly 60 is disposed in the pump body 42 within an exit flow path 70 that communicates between the pump bulb 40 and the cylinders 22. Squeezing the pump bulb 40 ejects the liquid through the exhaust valve assembly 60 along the exit flow path 70 and into the cylinders 22 to inflate the cylinders 22 and provide an erection.

The deflation valve assembly 62 is disposed in the pump body 42 in a deflation flow path 74 that is transverse to the exit valve assembly 60 and the inlet valve assembly 64. The deflation valve assembly 62 moves between the pads 50, 52 to allow the liquid in the cylinders 22 to drain or flow through the deflation flow path 74 back to the reservoir 24.

The inlet valve assembly 64 is disposed in the pump body 42 within an inlet flow path 76 that communicates between the reservoir 24 and the pump bulb 40. The inlet valve assembly 64 responds to suction on a downstream side (the pump bulb side) to allow liquid to be drawn from the reservoir 24, through the inlet flow path 76, and into the pump bulb 40.

The exhaust valve assembly 60 includes a ball valve 80 that is biased into contact with a surface 82 by a spring 84. The ball valve 80 is configured to be displaced from the surface 82 (thus compressing the spring 84) when liquid flows from the pump bulb 40 through the exhaust valve assembly 60 along the exit flow path 70 toward the cylinders 22. For example, compressing the pump bulb 40 ejects liquid from the pump bulb 40, which unseats the ball valve 80 from the surface 82 to allow the liquid to flow past the ball valve 80, along the exit flow path 70, through the deflation valve assembly 62 and into the cylinders 22. The expansion (or recovery) of the pump bulb 40 will create a downstream suction that draws liquid out of the reservoir 24, past the inlet valve assembly 64, and into the bulb 40. Subsequent pumping of the bulb 40 ejects the liquid from the bulb 40 into the cylinders 22. The spring 84 biases the ball valve 80 into contact with the surface 82 to block backflow of liquid from the cylinders 22 into the pump bulb 40. In this manner, the exhaust valve assembly 60 is provided as a one-way exhaust valve.

In one embodiment, the pump body 42 is an elastomeric chamber molded around the deflation valve assembly 62. The deflation valve assembly 62 operates to allow liquid to flow from the reservoir 24 through the inlet flow path 76 and into the pump bulb 40, and out the pump bulb 40 through the exit flow path 70 and into the cylinders 22 during inflation of the cylinders. The deflation valve assembly 62 operates to allow the user to deflate the cylinders 22. For example, in one embodiment pressing on the activation surfaces 50, 52 displaces the deflation valve assembly 62 toward the pad 50 to block the exit flow path 70, which allows liquid to flow from the cylinders 22 through the deflation flow path 74 in the pump body 42 and back to the reservoir 24, while bypassing the pump bulb 40.

The deflation valve assembly 62 includes a valve stem 90 extending between a first end 92 associated with the deflation pad 50, a second end 94 associated with the deflation pad 52, a spring 96 provided to bias the stem 90 relative to the pump body 42, and a crown 98 movably secured to the stem 90. In one embodiment, the spring 96 is a conical spring with one end of the spring wider than the other. Pushing on the deflation pads 50, 52 displaces the second end 94 of the stem away from the deflation pad 52. During the deflation process, movement of the stem 90 displaces the crown 98 into a lower portion of the deflation flow path 74, which blocks a portion of the exit flow path 70, and opens the deflation flow path 74 for the flow of liquid from the cylinders 22 back to the reservoir 24.

In a subsequent inflation process, squeezing the pump bulb 40 ejects liquid through the exhaust valve assembly 60, which displaces the crown 98 toward the pad 52 to open the exit flow path 70 between the pump bulb 40 and the cylinders 22.

The inlet valve assembly 64 includes a ball valve 100 that is biased into contact with a surface 102 by a spring 104. The ball valve 100 is configured to be displaced from the surface 102 (thus compressing the spring 104) when liquid is suctioned from the reservoir 24 as the pump bulb 40 expands, which draws liquid from the reservoir 24 into the pump bulb 40. Compressing the pump bulb 40 ejects liquid out of the pump bulb 40, which unseats the ball valve 80 from the surface 82 to allow the liquid to flow past the ball valve 80, along the exit flow path 70, through the deflation valve assembly 62 and into the cylinders 22. The expansion (or recovery) of the pump bulb 40 will create a downstream suction that draws liquid from the reservoir 24. The flow of the liquid out of the reservoir 24 pushes the ball valve 100 off of the seat 102, compressing the spring 104, to allow the liquid to flow through the inlet valve assembly 64 and into the bulb 40. Subsequent pumping of the bulb 40 ejects the liquid out of the bulb 40 into the cylinders 22, followed by a recovery of the pump bulb 40 that draws liquid from the reservoir 24 into the pump bulb 40. The spring 104 biases the ball valve 100 into contact with the surface 102 to block backflow of liquid out of the pump bulb 40 back to the reservoir 24.

Figure 4:
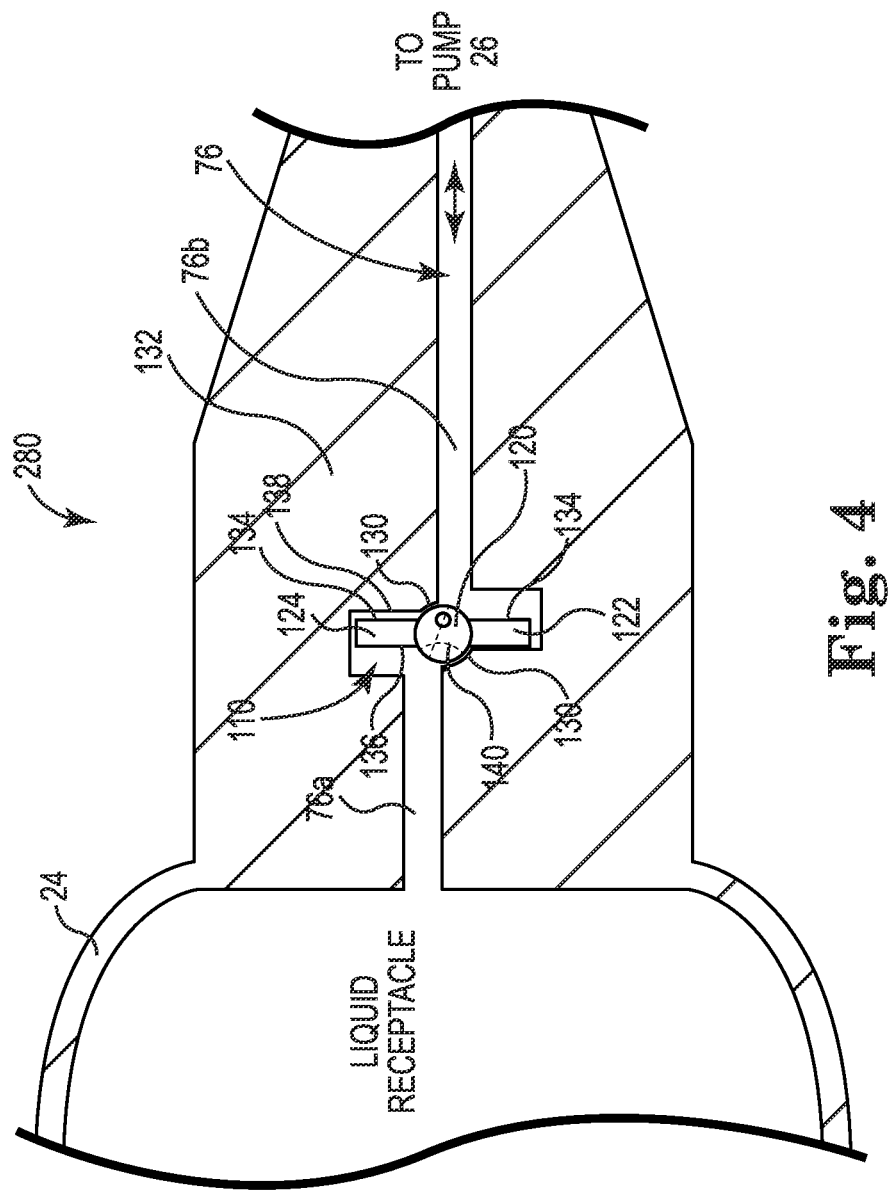
FIG. 4 is a cross-sectional view of a lockout valve assembly of the penile prosthetic illustrated in FIG. 1.

FIG. 4 is a cross-sectional view of the lockout valve assembly 28 integrated with the reservoir 24. The lockout valve assembly 28 includes a lockout valve 110 that is positioned between a first portion 76a of the inlet flow path 76 that communicates between the reservoir 24 and the assembly 28 and a second portion 76b of the inlet flow path 76 that communicates between the assembly 28 and the pump 26.

In one embodiment, the lockout valve 110 includes a core 120, an inlet flange 122 connected to and extending radially away from the core 120, and a lockout flange 124 connected to and extending radially away from the core 120. The inlet flange 122 and the lockout flange 124 extend radially away from the core 120. As illustrated, the inlet flange 122 is disposed on an opposite side (180 degrees) from the lockout flange 124. Other suitable orientations for the flanges 102, 104 are possible, particularly if accommodated by a complementary change in the pump body 42.

The core 120 is retained in rotational engagement within a seat 130 that is formed by a body 132 of the lockout valve assembly 28. The lockout valve 110 responds differently to suction applied downstream from the reservoir 24 than it responds to a pressure spike within the reservoir 24.

In one embodiment, the core 120 is spherical and has one or more flow channels formed on or through the spherical part. In one embodiment, the core 120 has a central cylinder shape that rotates within the body 132, where one or both ends of the cylindrical core is capped by a hemispherical shape.

Each of the inlet flange 122 and the lockout flange 124 has a pump face 134 that is located closer to the pump 26 than to the reservoir 24 and a reservoir face 136 that is located closer to the reservoir 24 than to the pump 26. The lockout valve 110 is configured such that contact between the pump face 134 of the lockout flange 124 and a wall 138 of the body 132 of the lockout valve assembly 28 prevents pressurized liquid from flowing from the reservoir 24 to the pump 26.

When suction is created downstream from the lockout valve 110 by the pump bulb 40, the low-pressure on the downstream side will draw the inlet flange 122 counter-clockwise as the core 120 rotates relative to the seat 130. The rotation of the core 120 and the inlet flange 122 operates to open a gate that allows liquid to flow from the reservoir 24 to the pump 26. For example, when the pump bulb 40 expands and creates a suction force on the inlet flow path 76, liquid is drawn from the reservoir 24 through the first portion 76a of the inlet flow path 76, through the core 120 and around the inlet flange 122, and through the second portion 76b of the inlet flow path 76 toward the pump 26 for inflation of the cylinders 22.

The lockout valve 110 includes an inflation channel 140 that is formed in the core 120. The seat 130 effectively seals the core 120 relative to the body 132, and in a closed position, seals the inflation channel 140 from communicating between the first portion 76a and the second portion 76b of the inlet flow path 76.

Rotation of the core 120 (with correlating rotation of the flanges 122, 124) aligns the inflation channel 140 with the first portion 76a and the second portion 76b of the inlet flow path 76 to allow liquid to flow from the reservoir 24 to the pump 26. Compression of the pump bulb 40 ejects any liquid in the pump bulb 40 through the exit flow path 70 and into the cylinders 22. The pump bulb 40 subsequently recovers by expanding, which creates a lower suction pressure on the pump side of the inlet flange 122. The low-pressure on the pump side of the inlet flange 122 causes the lockout valve 110 to rotate in a counterclockwise manner, which aligns the inflation channel 140 to form a conduit between the first portion 76a and the second portion 76b of the inlet flow path 76. The alignment of the inflation channel 140 within the inlet flow path 76 allows liquid to flow from the reservoir 24, through the core 120, and into the pump bulb 40. The repeated squeezing of the pump bulb 40 thus results in ejection of liquid into the cylinders 22 (when the pump bulb 40 is compressed) and suction of liquid into the pump bulb 40 (when the pump bulb 40 expands and recovers).

The lockout valve 110 responds differently to a pressure spike within the reservoir 24. As an example, a pressure spike can be created upstream from the lockout 110 by strenuous exercise or another force applied to the reservoir 24, which results in pressurized liquid being forced against the lockout flange 124. The force applied from the reservoir 24 to the lockout flange 124 pushes the flange 124 in a clockwise direction, which causes the lockout valve 110 to seal and close the second portion 76b of the inlet flow path 76.

Deflation of the cylinders 22 and directs a flow of liquid through the inlet flow path 76 toward the reservoir 24. The lockout valve 110 is positioned in the inlet flow path 76, which could block the return of the liquid into the reservoir 24. Embodiments of the lockout valve 110 provide mechanisms to allow liquid to flow through the lockout valve 110 and back into the reservoir 24.

Figure 5A:
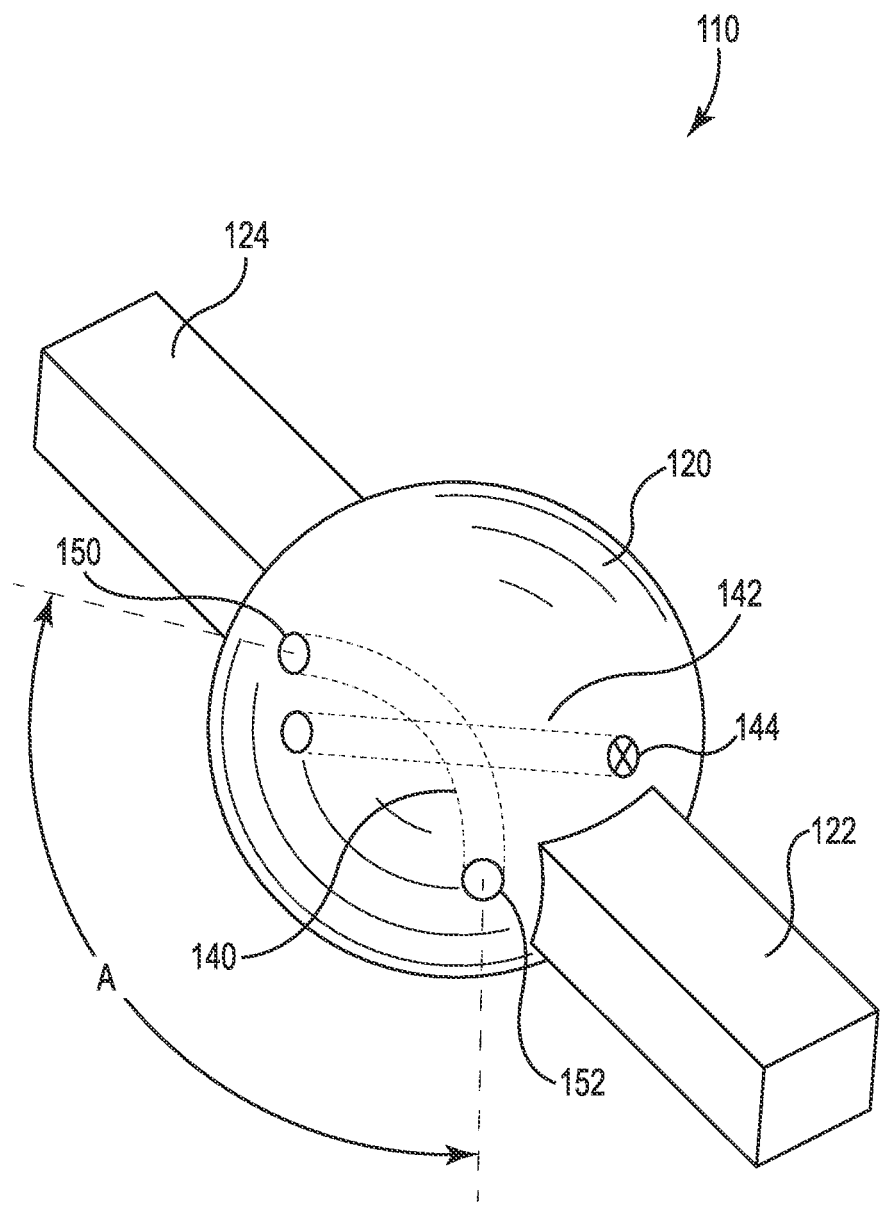
FIG. 5A is a perspective view.
Figure 5B:
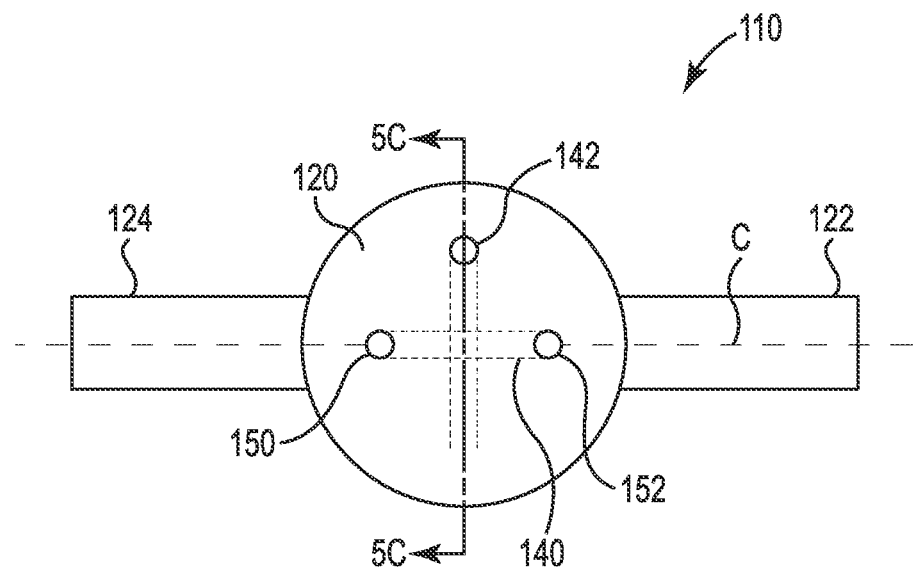
FIG. 5B is a front view.
Figure 5C:
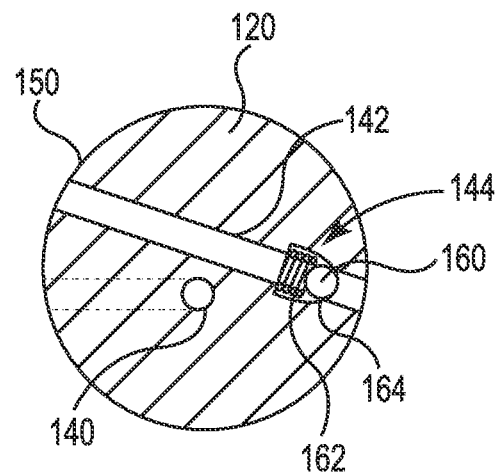
FIG. 5C is a cross-sectional view of the lockout valve illustrated in FIG. 4.

FIG. 5A is a perspective view, FIG. 5B is a front view, and FIG. 5C is a cross-sectional view of the lockout valve 110. The lockout valve 110 includes the inflation channel 140 and a deflation pathway 142.

The inflation channel 140 is formed through a portion of the core 120 and operates to allow liquid to flow from the reservoir 24 to the pump 26.

The deflation pathway 142 is formed in the core 120 separate from the inflation channel 140 and operates to allow liquid to flow from the cylinders 22 back into the reservoir 24. In one embodiment, the deflation pathway 142 extends entirely through a diameter of the core 120. In one embodiment, deflation pathway 142 is separate from the inflation channel 140 and is formed as a linear lumen through an entire diameter of the core 120. A one-way check valve 144 is disposed in the deflation pathway 142 to allow liquid to flow from the pump side back into the reservoir 24, and to prevent liquid flowing from the reservoir 24 through the deflation pathway 142.

In one embodiment, the inflation channel 140 is formed as a lumen in the core 120 that extends between an entrance hole 150 and an outlet hole 152. In one embodiment, the core is spherical and the entrance hole 150 is connected to the outlet hole 152, and both are formed in one single hemisphere (half) of the spherical core, for example on a side that faces the reservoir 24. In one embodiment, the inflation channel 140 is formed on a central equator C within one of two hemispheres of the core 120.

In one embodiment, the entrance hole 150 is separated from the outlet hole 152 by an angle A that measures in a range from 45-75 degrees. One suitable angle A measured between the entrance hole 150 and the outlet hole 152 is approximately 60 degrees.

The one-way check valve 144 is retained within the deflation pathway 142. In one embodiment, the one-way check valve 144 includes a ball valve 160 that is biased by a spring 162 against a seat 164 in the deflation pathway 142. The one-way check valve 144 is configured to allow liquid to displace the ball valve 160 and compress the spring 162, to allow liquid to flow through the deflation pathway 142. In contrast, liquid on the reservoir side of the lockout valve 110 is prevented from flowing through the deflation pathway 142 by a seal formed between the ball valve 160 and the seat 164.

The lockout valve 110 is suitably fabricated from metal or plastic. One suitable metal is stainless steel. Suitable plastics include acrylonitrile-butadiene-styrene, polyvinylchloride, nylon, or polypropylene to name several.

Figure 6A:
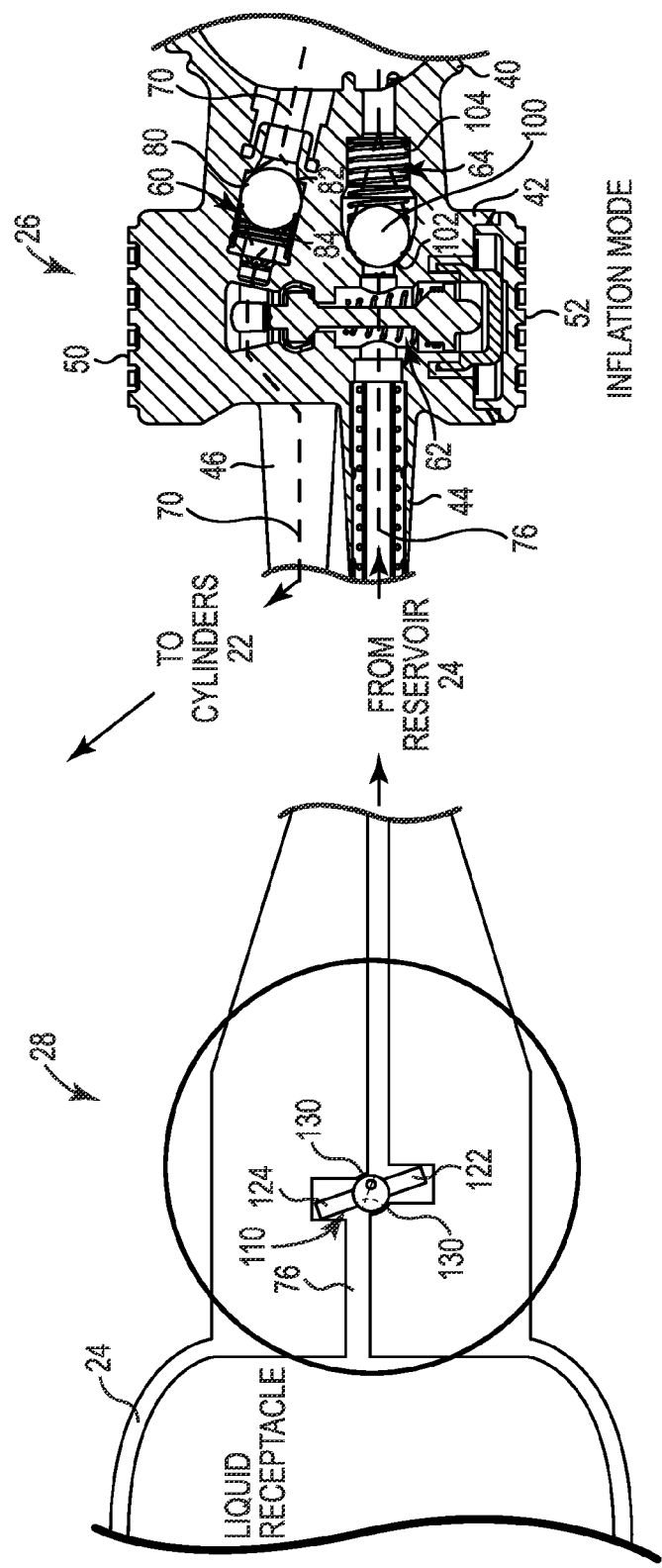
FIG. 6A is a cross-sectional view of portions of the penile prosthetic with the pump in an inflation mode for inflating the cylinders.

FIG. 6A is a cross-sectional view of the pump 26 and the lockout valve assembly 28 in an inflation mode and FIG. 6B is a view of the lockout valve assembly 28 with the pump 26 in the inflation mode.

The recovery of the pump bulb 40 creates suction inside the pump bulb 40 and in the second portion 76b of the inlet flow path 76. The suction in the downstream inlet flow path 76 creates a local low-pressure on the pump bulb face 134 of the inlet flange 122, which causes the inlet flange 122 and the core 120 to rotate in a counterclockwise direction. The rotation of the core 120 aligns the inflation channel 140 with the first portion 76a and with the second portion 76b of the inlet flow path 76. In this manner, the inlet flow path 76 is open and the suction from the pump bulb 40 draws liquid from the reservoir 24, past the ball 100, and into the pump bulb 40. Subsequent squeezing or compression of the pump bulb 40 ejects the liquid in the pump bulb 40 through the exit flow path 70 and into the cylinders 22.

FIG. 7A is a cross-sectional view of the pump 26 and the lockout valve assembly 28 in a deflation mode and FIG. 7B is a view of the one-way check valve 144 of the core 120 of the lockout valve 110 in the deflation mode.

The user is instructed to touch the deflation pads 50, 52 and apply a force that displaces the stem 90 of the deflation valve assembly 62 to open the deflation flow path 74. Movement of the stem 90 results in the crown 98 being displaced to close the exit flow path 70 and to open the deflation flow path 74 between the cylinders 22 and a reservoir 24. The ball valve 80 is forced onto the seat 82 by the pressure of the liquid in the deflation flow path 74.

The pressure of the liquid in the deflation flow path 74 pushes on the pump bulb face 134 of the inlet flange 122 to close the lockout valve 110 and open the one-way check valve 144. The pressure of the liquid in the deflation flow path 74 pushes the ball 160 off of the seat 164, which allows the liquid to flow through the core 120 of the lockout valve 110 from the second portion 76b to the first portion 76a of the flow path 76. In this manner, liquid is allowed to flow from the cylinders 22 back to the reservoir 24 through the closed lockout valve 110.

FIG. 8 is a vertical cross-sectional view of the lockout valve assembly 28 providing the penile prosthetic 20 (FIG. 1) with a lockout mode. The pump 26 is at steady state with the lockout valve 110 providing a lockout mode that prevents unintended pressure spikes applied to the reservoir 24 from delivering a flow of liquid into the cylinders 22.

When the penile prosthetic system 20 is implanted into the user, the cylinders 22 are located in the penis, the reservoir 24 is typically implanted in the abdomen, and the pump 26 is implanted in the scrotum. In the steady state, the liquid is retained in the reservoir 24 and the cylinders 22 are flaccid. Strenuous physical activity or outside pressure applied to the abdomen has the potential to create a pressure spike in the reservoir 24, which could undesirably cause liquid to flow from the reservoir 24, through the pump bulb 40, and into the cylinders 22. The undesirable inflation of the cylinders 22 that arises from a large pressure applied to the reservoir 24 is referred to as autoinflation.

In one embodiment, the lockout valve 110 provides a lockout feature to prevent autoinflation of the cylinders 22. An unexpected pressure spike applied to the reservoir 24 will pressurize the liquid on the reservoir side of the lockout valve 110. The pressurized liquid applies a force against the reservoir face 136 (FIG. 4) of the lockout flange 124. The increased pressure applied on the reservoir face 136 of the lockout flange 124 forces the pump bulb face 134 (FIG. 4) of the valve 110 against the wall 138 of the body 132 to create and maintain a seal that closes the inlet flow path 76. The core 120 is sealed against the seat 130 and the reservoir face 135 of the inlet flange 122 is pressed against the body 132 of the lockout valve assembly 28. Consequently, the pressurized liquid on the reservoir side of the lockout valve 110 is unable to flow past the lockout valve assembly 28 toward the pump 26. In this manner, the lockout valve 110 provides an auto-lock mode for the pump 26.

Figure 9:
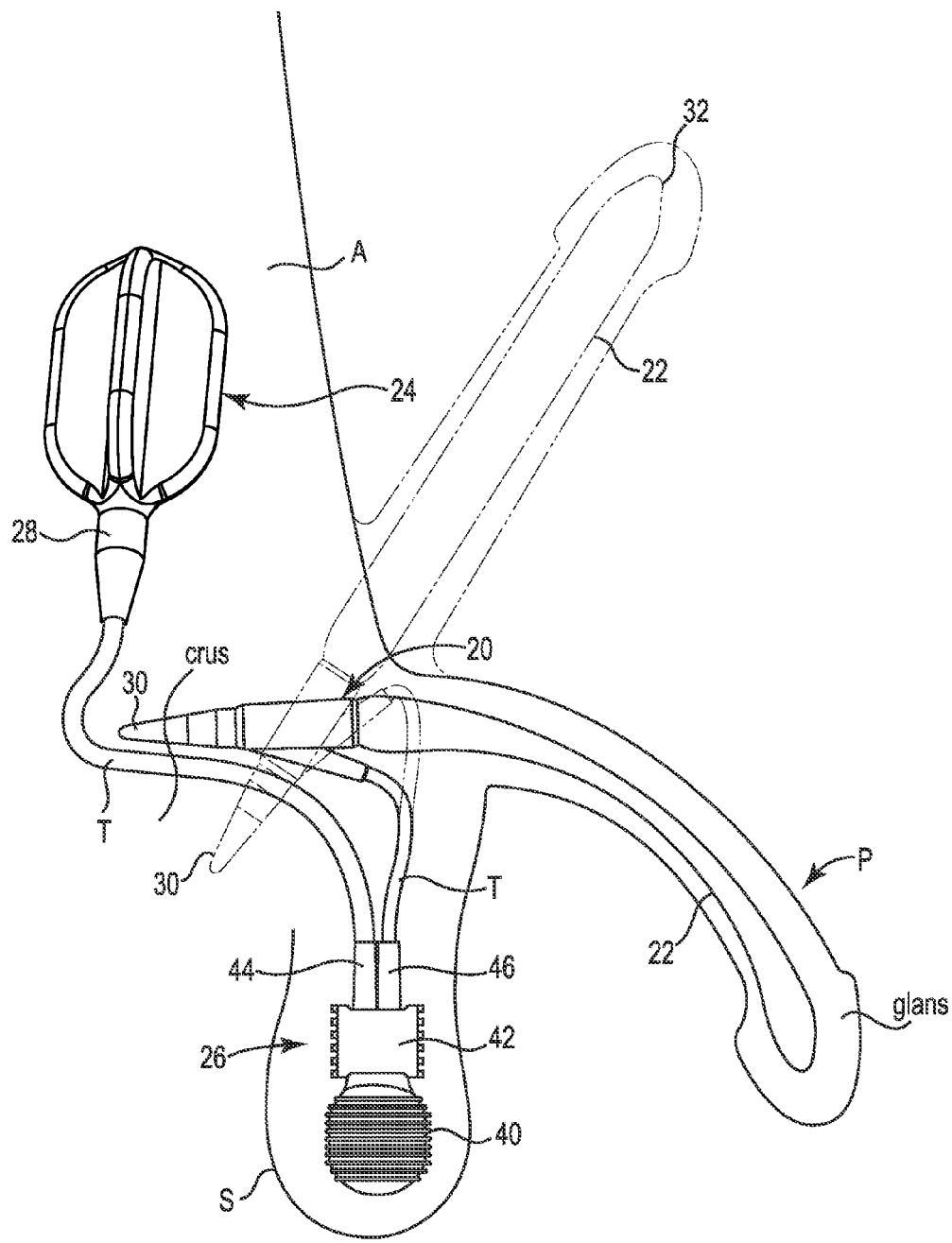
FIG. 9 is a schematic view of one embodiment of the penile prosthetic illustrated in FIG. 1 implanted into a user.

FIG. 9 is a schematic side view of the penile prosthetic 20 implanted in a user. The cylinders 22 are implanted in the penis P with the proximal end 30 inserted near the crus and the distal end 32 implanted within the glans. The reservoir 24 is implanted within the abdomen and the pump 26 is implanted within the scrotum S.

The penile prosthetic 20 is operable consistent with the description above to inflate the cylinders 22 to achieve an erect state (as described in FIGS. 5A and 5B above) and to drain liquid out of the cylinders 22 to return the penis P to a flaccid state. The lockout valve assembly 28 is responsive to pressure conditions in the reservoir or the pump 26. Specifically, the lockout valve assembly 28 operates to allow the pump 26 to draw liquid from the reservoir 24 and deliver the liquid into the cylinders 22 to provide the user with an erection. The lockout valve assembly 28 also operates to allow the cylinders 22 to be deflated by draining the liquid from the cylinders 22 back into the reservoir 24. The lockout valve assembly 28 operates to prevent the unintended pressurization of liquid in the reservoir 24 from undesirably, and unintentionally, inflating the cylinders 22 and causing an unintended erection.

In one embodiment, the pump 26 provides a one-touch release mechanism that allows the cylinders 22 to easily and quickly deflate by an initial, nearly instantaneous activation of the surfaces 50, 52 as opposed to the user applying prolonged pressure (e.g., more than three seconds of applied pressure) to the surfaces 50, 52. Thus, a quick and convenient approach is provided for the rapid deflation of the inflated cylinders 22, which is appreciated by users with limited dexterity.

Referring to FIGS. 6A-6B and FIG. 9, one embodiment of the lockout valve 110, the exhaust valve assembly 60, and the deflation valve assembly 62 has this sequence of inflation operations: The Penis P is flaccid and reservoir 24 contains liquid. The lockout valve 110 is closed, the exhaust valve assembly 60 is closed, and the deflation valve assembly 62 is open (if the penis had been previously made erect). The pump bulb 40 is squeezed and the exhaust valve assembly 60 opens as the ball valve 80 compresses the spring 84 to allow any liquid in the pump bulb 40 to leave the pump bulb 40 and flow to the cylinders 22. Liquid flowing toward the cylinders 22 will push the crown 98 downward to close the deflation valve assembly 62, thus opening the exit flow path 70 to the cylinders 22. The deflation valve assembly 62 is closed and remains closed during subsequent pumping of the pump bulb 40 that drives liquid out of the pump bulb 40 through the exhaust valve assembly 60 and into the penile cylinders 22. When the pump bulb 40 is released during pumping action, the bulb volume expands to create suction. The suction in the pump bulb 40 creates a local low pressure on the pump bulb face 134 of the lockout valve 110, which causes the lockout valve 110 to rotate counterclockwise and open. Liquid is drawn out of the reservoir 24 through the lockout valve 110 to the pump bulb 40. The exhaust valve assembly 60 is closed when the pump bulb 40 is released during pumping action, and remains closed until the bulb 40 is squeezed. The deflation valve assembly 62 remains closed during the inflation of the cylinders 22. Squeezing the bulb 40 ejects the liquid from the bulb 40 and through the exhaust valve assembly 60.

Referring to FIGS. 7A-7B and FIG. 9, one embodiment of the lockout valve 110, the exhaust valve assembly 60, and the deflation valve assembly 62 has this sequence of deflation operations: The penis P is erect and the cylinders 22 are filled with liquid. The lockout valve 110 is closed, the exhaust valve assembly 60 is closed, and the deflation valve assembly 62 is closed. The user presses on the surfaces 50, 52 to open the deflation valve assembly 62, and the liquid flows from the penile cylinders 22 transversely through the deflation valve assembly 62 along the deflation flow path 74 in the pump body 42 toward the reservoir 24. The pressure in the liquid opens the one-way valve 144 by pushing the ball 160 off of the seat 164 to allow the liquid in the cylinders 22 to flow back into the reservoir 24. After the liquid flows back into the reservoir 24, the one-way valve 144 closes and the lockout valve 110 is closed and the exhaust valve assembly 60 is closed.

Referring to FIG. 4 and FIGS. 8-9, one embodiment of the lockout valve 110 and the pump 26 has this sequence of anti-autoinflation operations: The penis P is flaccid and the reservoir 24 is filled with liquid. The lockout valve 110 is closed, the exhaust valve assembly 60 is closed, and the deflation valve assembly 62 is closed. The reservoir 24 is pressurized, either through a natural body function (e.g., sneezing or coughing) or through an external force (e.g., strenuous exercise or the user pressing against a table edge). The pressurized liquid in the reservoir 24 applies a force against the reservoir face 136 of the lockout flange 124. The increased pressure applied on the reservoir face 136 of the lockout valve 110 forces the pump bulb face 134 of the valve 110 against the wall 138 of the body 132 to create and maintain a seal that closes the inlet flow path 76. Consequently, the pressurized liquid on the reservoir side of the lockout valve 110 is unable to flow into the second portion 76*b* of the inlet flow path 76 and is prevented from entering the pump bulb 40.

FIG. 10 is a schematic cross-sectional view of one embodiment of an assembled penile prosthetic 200. The penile prosthetic 200 is provided to the healthcare facility in several parts that are assembled by a surgeon into a working unit during implantation. As manufactured, the penile prosthetic 200 includes cylinders (not shown, but similar to cylinders 22 of FIG. 1) that are implantable into a penis, a reservoir 240, the pump 26 described above that is attachable between the cylinders and the reservoir 240, for example by suitable implantable tubing T, and a lockout valve assembly 280. The reservoir 240 is similar to the reservoir 24 described above and includes a receptacle sized to hold a volume of liquid that is employed to inflate the cylinders. The lockout valve assembly 280 includes the lockout valve 110 located in the inlet flow path 76.

In one embodiment, the lockout valve assembly 280 is separate from the reservoir 240 and separate from the pump 26, and is attachable to each of these by appropriate tubing T. The lockout valve assembly 28 described above is integrated as one monolithic piece with the reservoir 24, and the lockout valve assembly 280 of FIG. 10 is a separate unit attached between the reservoir 240 and the pump 26.

Figure 11A:
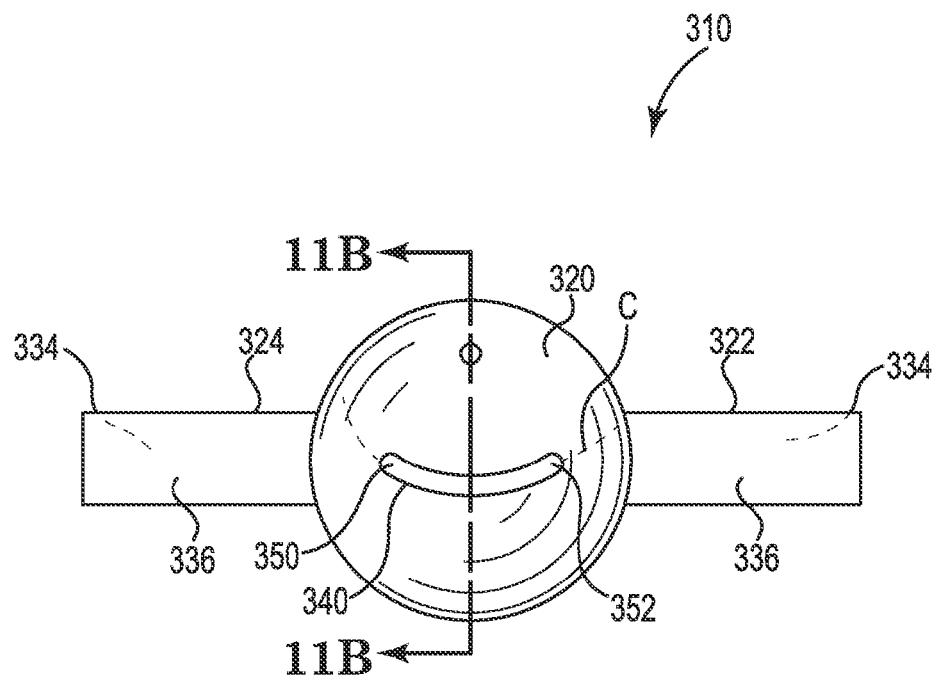
FIG. 11A is a front view and FIG. 11B is a side view of one embodiment of a lockout valve.
Figure 11B:
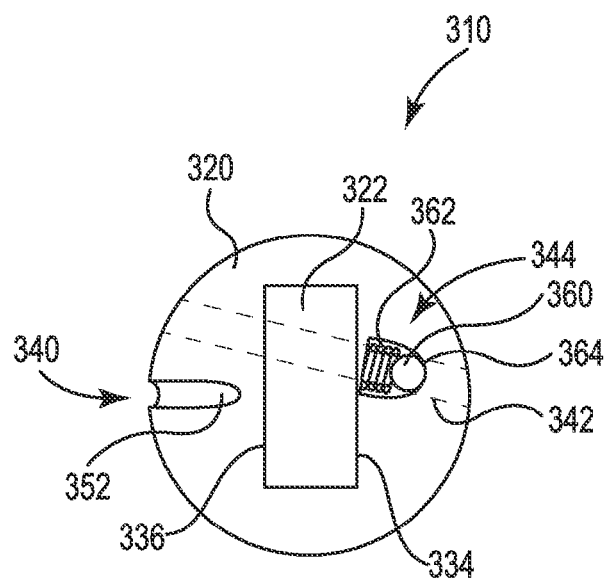

FIG. 11A is a front view and FIG. 11B is a side view of one embodiment of a lockout valve 310 suitable for use in the lockout valve assembly 28 (FIG. 4) or the lockout valve assembly 280 (FIG. 10).

The lockout valve 310 includes a core 320, an inlet flange 322 connected to and extending radially away from the core 320, and a lockout flange 324 connected to and extending radially away from the core 320. The core 320 is suitably fabricated as a spherical part, or as a cylindrical part having hemispherical cap portions as described above. As illustrated, the inlet flange 322 is disposed on an opposite side (180 degrees) from the lockout flange 324. Other suitable orientations for the flanges 322, 324 are possible, particularly if accommodated by a complementary change in the body of the lockout valve assembly.

Each of the inlet flange 322 and the lockout flange 324 has a pump bulb face 334 and a reservoir face 336. When assembled into the lockout valve assembly, the pump bulb face 334 is located closer to the pump bulb 40 than to the reservoir 24, and the reservoir face 336 is located closer to the reservoir 24 than to the pump bulb 40. In one embodiment, a height of the inlet flange 322 is the same as a height of the lockout flange 324, and each of the flanges 322, 324 has a height that is less than a diameter of the spherical part 320.

The lockout valve 310 includes an inflation channel 340 and a deflation pathway 342.

The inflation channel 340 is formed through a portion of the spherical part 320 and operates to allow liquid to flow from the reservoir 24 to the pump 26.

The deflation pathway 342 is formed in the spherical part 320 separate from the inflation channel 340 and operates to allow liquid to flow from the cylinders 22 back into the reservoir 24. In one embodiment, the deflation pathway 342 extends entirely through a diameter of the spherical part 320. A one-way check valve 344 is disposed in the deflation pathway 342 to allow liquid to flow from the pump side back into the reservoir 24, and to prevent liquid flowing from the reservoir 24 through the deflation pathway 132.

The inflation channel 340 that functions in a manner similar to the inflation channel 140 described above in FIGS. 5A-5C. In one embodiment, the inflation channel 340 is a groove that is formed in an exterior surface of the core 320 so that the channel is exposed on the exterior surface. The channel 340 (or groove 340) is formed in the spherical part 320 along a central equator C on the reservoir face side of the valve 310. The groove 340 extends from an entrance 350 to an exit 352 for about 60 degrees along the equator C of the spherical part 320, or between the 2 o'clock position and the 4 o'clock position when viewed from above.

One suitable shape of the groove 344 is a semi-circular cut made in the exterior surface of the spherical part 320, for example by a ball-end mill to provide the groove 340 a convex curvature along the exterior surface of the spherical part 320 and with a concave curvature in longitudinal cross-section.

The one-way check valve 344 is retained within the deflation pathway 342. In one embodiment, the one-way check valve 344 includes a ball valve 360 that is biased by a spring 362 against a seat 364 in the deflation pathway 142. The one-way check valve 344 operates to allow liquid to displace the ball valve 360 (thus compressing the spring 362) to allow liquid to flow through the deflation pathway 342 back to the reservoir 24. In contrast, liquid on the reservoir side of the lockout valve 110 is prevented from flowing through the deflation pathway 342 by a seal formed between the ball valve 360 and the seat 364.

The lockout valve 320 is suitably fabricated from metal or plastic. One suitable metal is stainless steel. Suitable plastics include acrylonitrile-butadiene-styrene, polyvinylchloride, or polypropylene to name several.

Embodiments provide a penile prosthetic having a lockout valve assembly that is provided separate from the pump and reservoir and configured to prevent a stream of pressurized liquid from undesirably flowing from the reservoir directly to the cylinders.

Although specific embodiments have been illustrated and described in this disclosure, it will be appreciated by those of ordinary skill in the art that a variety of alternate and/or equivalent implementations may be substituted for the specific embodiments shown and described without departing from the scope of this disclosure. This application is intended to cover any adaptations or variations of the above-disclosed medical devices. Therefore, it is intended that this invention is limited only by the claims and their equivalents.

What is claimed is:

1. A lockout valve assembly of an implantable penile prosthetic, the lockout valve assembly comprising:
a body attachable between a reservoir and a pump of the implantable penile prosthetic; and
a lockout valve positioned in an inlet flow path between the reservoir and the pump and including:
a core retained in rotational engagement within a seat formed inside the body,
an inlet flange connected to and extending radially away from the core, and
a lockout flange connected to and extending radially away from the core,
an inflation channel formed through a portion of the core,
a deflation pathway separate from the inflation channel and formed through a diameter of the core, and
a one-way check valve disposed in the deflation pathway of the core,
wherein the lockout valve is configured such that contact between a pump face of the lockout flange and a wall of the body prevents pressurized liquid from flowing from the reservoir to the pump, and such that low pressure downstream of the lockout valve created by suction from the pump draws the inlet flange counterclockwise as the core rotates relative to the seat, and
wherein rotation of the core and the inlet flange operates to open a gate that allows liquid to flow from the reservoir to the pump.

2. The lockout valve assembly of claim 1, wherein the body is separate from the reservoir and attachable to the reservoir with a first section of tubing and attachable to the pump with a second section of tubing.

3. The lockout valve assembly of claim 1, wherein the body is monolithically integrated with the reservoir and attachable to the pump with a section of tubing.

4. The lockout valve assembly of claim 3, wherein the body is located between a liquid receptacle of the reservoir and the section of tubing.

5. The lockout valve assembly of claim 1, wherein each of the inlet flange and the lockout flange has a pump face that is located closer to the pump than to the reservoir and a reservoir face that is located closer to the reservoir than to the pump.

6. The lockout valve assembly of claim 5, wherein the inflation channel is formed in the core of the lockout valve between the reservoir face of the inlet flange and the reservoir face of the lockout flange.

7. The lockout valve assembly of claim 1, wherein the inflation channel is a lumen formed within the core, the lumen extending between an entrance hole and an outlet hole.

8. The lockout valve assembly of claim 7, wherein the entrance hole is separated from the outlet hole by an angle that measures in a range from 45-75 degrees.

9. The lockout valve assembly of claim 1, wherein the core is spherical and the inflation channel is a lumen formed within a single hemisphere of the spherical core, with the lumen extending between an entrance hole located on the single hemisphere and an outlet hole located on the single hemisphere.

10. The lockout valve assembly of claim 1, wherein the inflation channel is a groove formed in an exterior surface of the core.

11. The lockout valve assembly of claim 1, wherein the core is spherical.

12. The lockout valve assembly of claim 1, wherein the inflation channel includes an outlet hole that is blocked from the inlet flow path by a seat formed in the body of the lockout valve assembly and opened to the inlet flow path by rotation of the core of the lockout valve.

13. The lockout valve assembly of claim 1, wherein the deflation pathway is a lumen formed linearly through the core.

14. The lockout valve assembly of claim 1, wherein the one-way check valve is a ball valve that is biased by a spring disposed in the deflation pathway of the core.

15. The lockout valve assembly of claim 1, further comprising:
a deflation valve assembly disposed in the pump.

16. The lockout valve assembly of claim 15, wherein the deflation valve assembly has a stem that is movable and a crown that is separate from and movable relative to the stem.

17. A lockout valve assembly of an implantable penile prosthetic, the lockout valve assembly comprising:
a body attachable between a reservoir and a pump of the implantable penile prosthetic; and
a lockout valve positioned in an inlet flow path between the reservoir and the pump, the lockout valve including:
a core retained in rotational engagement within a seat formed inside the body,
an inlet flange connected to and extending radially away from the core, and
a lockout flange connected to and extending radially away from the core,
an inflation channel formed through a portion of the core,
a deflation pathway that is separate from the inflation channel and formed through a diameter of the core, and
a one-way check valve disposed in the deflation pathway of the core;
wherein rotation of the core and the inlet flange operates to open a gate that allows liquid to flow from the reservoir to the pump.

* * * * *